United States Patent [19]
Sadjadi et al.

[11] Patent Number: 5,483,066
[45] Date of Patent: Jan. 9, 1996

[54] POLARIZATION DIVERSE INFRARED OBJECT RECOGNITION SYSTEM AND METHOD

[75] Inventors: Firooz A. Sadjadi, Minneapolis; Stephen M. Sohn, Shoreview, both of Minn.

[73] Assignee: Loral Corporation, New York, N.Y.

[21] Appl. No.: 257,255

[22] Filed: Jun. 8, 1994

[51] Int. Cl.$^6$ .................................................. G01J 5/58
[52] U.S. Cl. ..................................... 250/338.1; 250/330
[58] Field of Search ........................... 356/369; 250/330, 250/332, 338.1

[56]  References Cited

U.S. PATENT DOCUMENTS

| | | | |
|---|---|---|---|
| 4,560,279 | 12/1985 | Kouns | 356/369 |
| 5,138,162 | 8/1992 | Hacskaylo | 250/330 |
| 5,416,324 | 5/1995 | Chun | 250/341.3 |

OTHER PUBLICATIONS

Werner Frei, Manbir Singh and Tsutomu Shibata, "Digital image change detection." *Optical Engineering*, vol. 19, No. 3 (May/Jun. 1980) pp. 331–338.

*Primary Examiner*—Constantine Hannaher
*Attorney, Agent, or Firm*—John B. Sowell; Glenn W. Bowen

[57] ABSTRACT

A polarization diverse image sensor identifies different objects of green vegetation and produces a vegetation index of such vegetation. The sensor defines the degree, angle and intensity of polarization. This information is stored in a memory for producing an image memory map of the polarized pixel data. Differential pixel data is computed and then employed to generate a new polarization difference image which is further processed by histogramming slices of the new image to obtain a segmented image of the green vegetation. The attributes of the segmented image are then compared with segmented data which was previously stored in a model base library to obtain a match or no match of the identification of the green vegetation. If match is obtained, a controller issues control signals which controls the spray heads and chemicals carried on a moving spray platform. However, if no match is obtained, the original raw data is labeled, formatted and stored in the model base library as reference data. The generated data is stored in the memory base library for further analysis or for use in real time control of a utilization device that treats the green vegetation previously that was recognized and identified.

13 Claims, 4 Drawing Sheets 5,483,066

POLARIZATION DIVERSE INFRARED OBJECT RECOGNITION SYSTEM AND METHOD

BACKGROUND OF THE INVENTION

1. Related Applications

The present invention relates to our copending U.S. application Ser. No. 08/257,257, filed 25 Jul. 1994, for a "Smart Weed Recognition/Classification System".

2. Field of the Invention

The present invention relates to automatic target recognition (ATR) systems. More particularly, the present invention relates to an object or vegetation recognition system which employs a polarization sensitive infrared detector sensor.

3. Description of the Prior Art

Automatic target recognition (ATR) systems are known. Systems for recognition and application of chemicals to green vegetation are also known. In both types of system, various means for detection have been employed. The extent of the accuracy and reliability of the detection systems depends on the type and amount of the information that is available which describes a scene or area of the target object and its background environment. While both infrared sensors and polarization-sensitive infrared sensors are known, there are no known automatic recognition systems which fully exploit sets of polarization-sensitive information from a scene to describe and recognize green vegetation by type, size, color, and/or attributes which would enable concurrent or subsequent treatment of the vegetation.

Accordingly there is an unsatisfied need for an object recognition that is highly accurate, extremely reliable and can be operated and programmed at low cost to detect green vegetation as well as other types of objects which emit energy in the infrared range.

SUMMARY OF THE INVENTION

It is a principal object of the present invention to provide an automatic target recognition system which is adapted to recognize and classify green vegetation as the object being sensed.

It is a principal object of the present invention to provide a system and a method for recognizing objects employing a plurality of polarization attributes or features which define the scene containing an object or objects.

It is another principal object of the present invention to encode a plurality of polarization-attributes or features of a scene to be analyzed into analog TV color signals for conversion into frames or maps of information for further processing and analysis.

It is a principal object of the present invention to convert plural sets of polarization attributes into digital image data and to enhance the digital image data by segmentation into subregions and regions for extraction of the attributes which define the objects to be recognized.

It is a general object of the present invention to provide an improved green vegetation recognition and identification system for use in real time applications of chemicals or for generating historic archival information for green vegetation analysis.

According to these and other objects of the present invention, there is provided an automatic green vegetation recognition system which comprises a polarized-diverse infrared imaging sensor for generating a set of a plurality of features which define the degree, angle, and intensity of polarization of the scene to be analyzed.

The scene is stored in a memory map as an image of polarized digital pixel data. Differential pixel data is computed and then employed to generate a new polarization difference image which is processed by histogramming slices of the new image to obtain a segmented image of the green vegetation to be analyzed. The attributes of the segmented image are compared with segmented data previously stored in a model base library or archive to obtain a match or no match decision. When a match is obtained, a controller may issue control signals which control the spray heads of chemicals carried on a moving spray platform in real time. When no match is obtained, the original raw data may be labelled and formatted and stored in the model base library for future use as reference data.

DETAILED DESCRIPTION OF THE PREFERRED EMBODIMENTS

Figure 1:
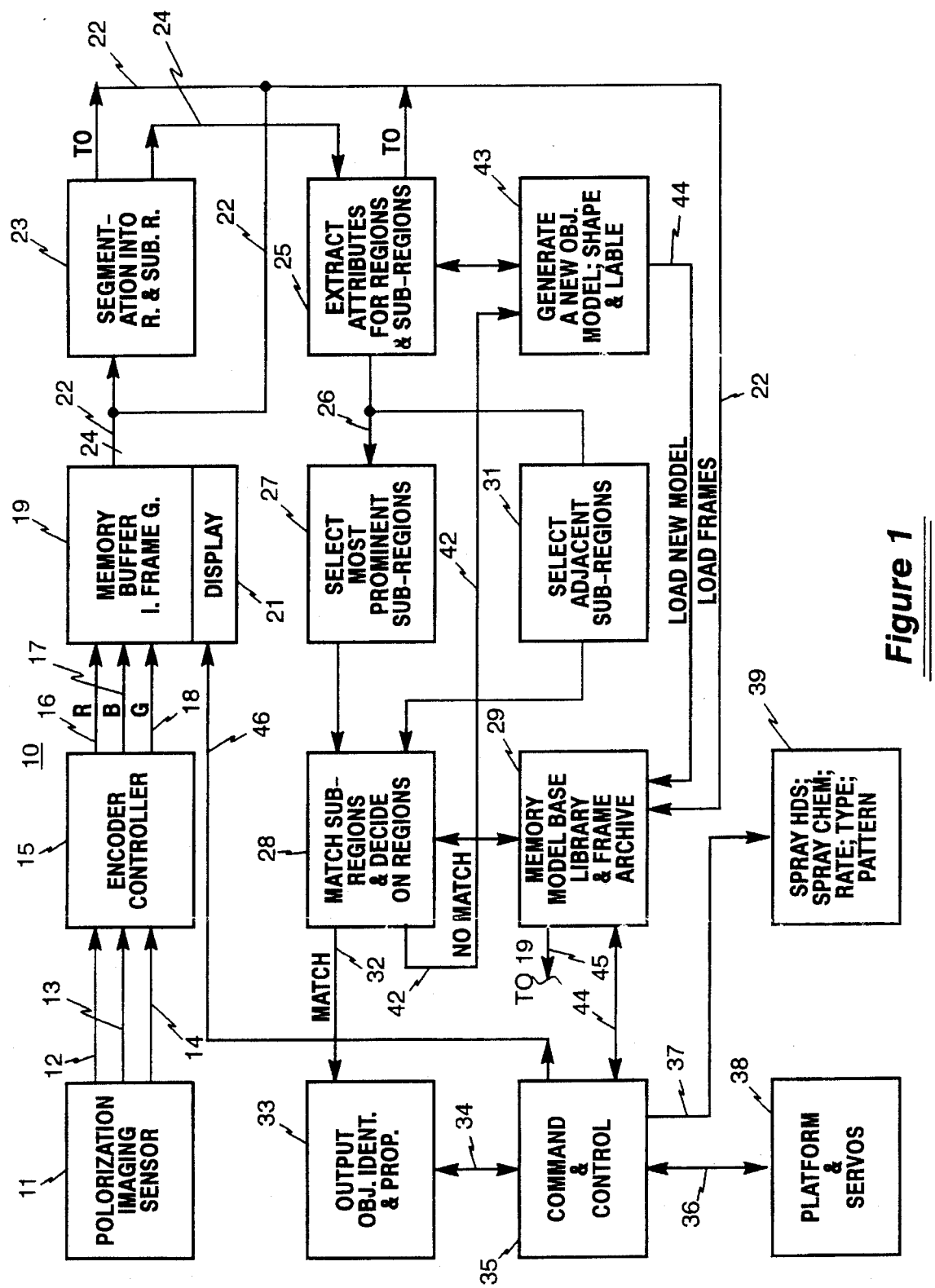
FIG. 1 is a schematic block diagram of the present invention automatic object recognition system adapted to recognize green vegetation.

Refer now to FIG. 1 showing an automatic polarization diverse object recognition system 10. The input signals for the present invention system are generated by a polarization imaging sensor 11 adapted to generate a set of at least three separate and distinct polarization features namely, the degree, the angle, and the intensity of polarization. These three selected features may be generated by placing polarization filters in front of separate CCD arrays, or by modifying a camera having three CCD arrays already installed in the camera or by purchasing a special polarization camera from a vendor such as Physics Innovations.

The polarization imaging sensor 11 is preferably an infrared polarization-sensitive sensor that generates signals from the red and near-red infrared spectrum having a wavelength lying between 630 and 870 nanometers that has been found desirable for recognizing green vegetation as well as various and sundry man-made objects such as aircraft, vehicles, and buildings.

The polarization imaging sensor 11 is adapted to provide an intensity signal on line 12 and a angle of polarization signal on line 13 and a degree of polarization signal on line 14 which are applied to an encoder controller 15. The output of the encoder controller 15 generates three typical red, blue, and green television compatible signals on lines 16 to 18 which are applied and stored in a memory buffer and frame grabber 19. The memory buffer 19 also has coupled thereto a display 21 which will display memory maps of frames stored in memory 19. The output of the memory buffer on line 22 comprises 24 digital bits for each pixel for defining the three colors with eight digital bits each. The digital frame of information comprising an image of the scene produced by the sensor 11 is processed by a segmentation operation into regions and subregions at block 23. The output of the segmentation operation on line 24 is applied as an input to block 25 which performs an attribute extraction operation on each of the separate subregions and regions within the segmented digital memory map.

Once the attributes are extracted in block 25, the most prominent subregions are selected at block 27 via line 26 for matching and comparison in block 28 with the information stored in a memory model base library and frame archive 29. To speed up the operation of achieving a match, the most prominent subregions are employed to achieve a preliminary match, and when that match occurs, the selected adjacent subregions from block 31 are then processed to obtain a final match. If a final match is achieved, an output signal on line 32 to block 33 causes a signal on line 34 to be generated which identifies the object (subregion) and properties of the subregion object so that the command and control block 35 is enabled to generate output signals on lines 36 and 37 used to control the blocks 38 and 39 labeled platform and servos and spray heads, spray chemicals, rate, type; and pattern respectively. If the system 10 is operating in a real time mode to spray green vegetation, the active signals on line 36 and 37 will accomplish this end. However, if the system 10 is an archival mode the information necessary to control the blocks 38 and 39 is stored in the archival memory 29 via line 41.

In the event that no match was obtainable at block 28, a signal on line 42 indicative of no match is coupled to the block 43 entitled generate a new object model and its shape and label the model, which information is stored via line 44 into the archive memory 29.

The polarization recognition system 10 is capable of loading information from memory buffer 19 via line 22 into the memory model base library 29. Further, the information being processed in the segmentation block 23 may also be outputted onto line 22 and stored in the model base library 29. Further, the information which is being processed in block 25 is also available on line 22 for storage into the model base library under control of the command control unit 35 via line 41. If this information in the model base library for any reason needs to be displayed, it is first transferred to the memory buffer and frame grabber 19 via line 45 under the control of the command controller 35 which controls the display 21 via line 46. Having explained the basic operation of the functional blocks in FIG. 1, it will be understood that there are three distinct modes of operation. The automatic teaching mode permits the system to learn the definition and description of objects to be recognized and store this information in the memory base model 29. Further, the information once stored in the library may be employed to match information and areas being examined in real time to obtain a match that results in generating control signals to the moving platform and servos at block 38 and also applying signals which will selective spray heads to spray selective chemicals on selective areas. In a third or diagnostic mode, the command and control unit may be employed to examine the results being produced in each of the functional blocks and to modify and control the processing operations to further optimize the results of the present system.

Figure 2:
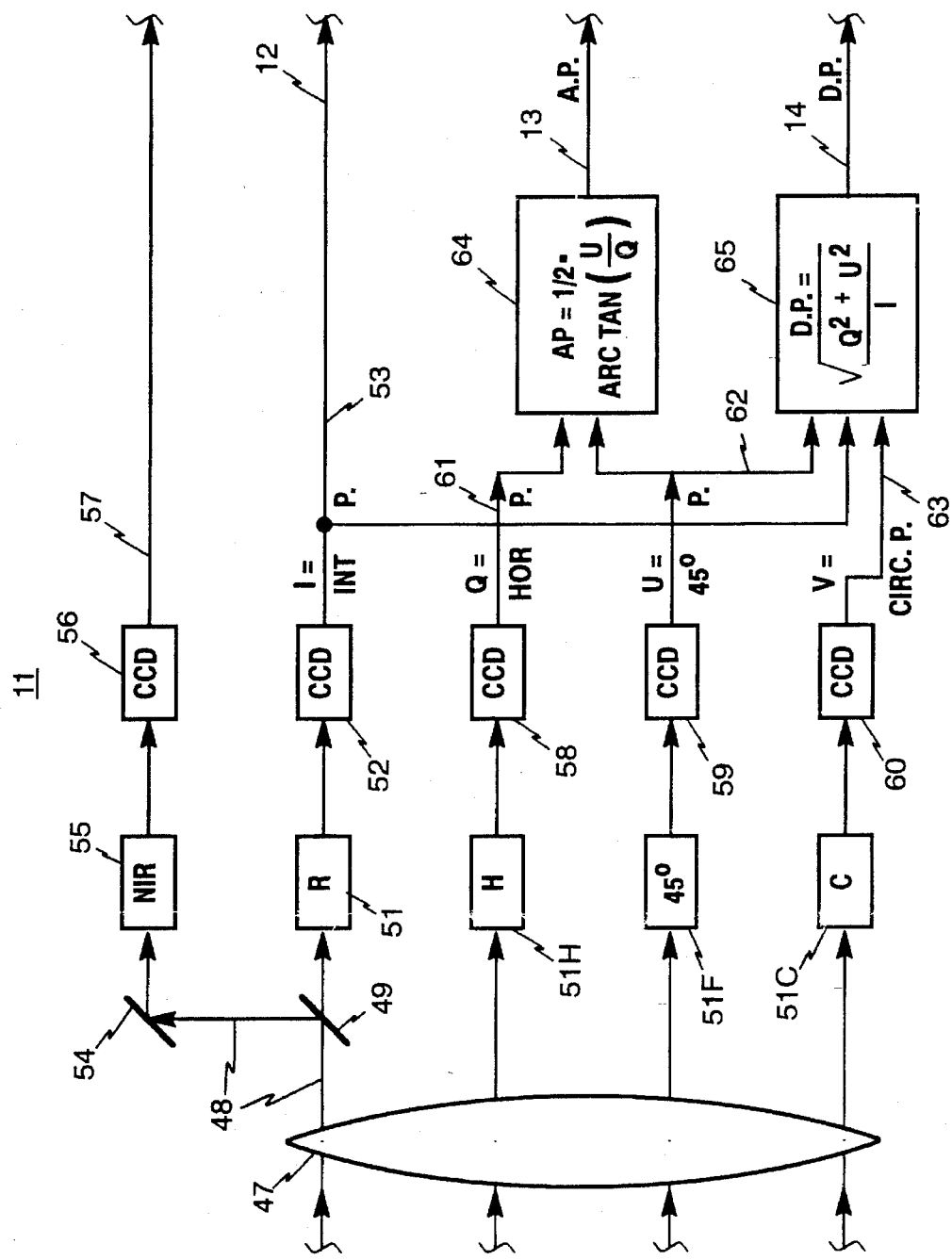
FIG. 2 is a schematic drawing of a polarization-sensitive infrared sensor adapted to generate four features of polarization which may be used in the present invention.

Refer now to FIG. 2 showing a schematic drawing of a polarization-sensitive infrared sensor 11 that is adapted to generate the set of polarization feature signals on lines 12, 13, and 14 described hereinbefore with reference to FIG. 1. While this particular sensor 11 employs an objective lens 47 for directing an image of the area to be viewed onto 4 CCDs to obtain the three sets of information, the fourth CCD has been added in the preferred embodiment sensor to obtain a near infrared output signal as well as an infrared output signal on line 12 to produce a vegetation index signal computed as the ratio of NIR/R. In the sensor shown in FIG. 2, light entering path 48 passes through a half silvered mirror 49 and an infrared filter 51 to be focused on a first CCD 52. The infrared output (R) on line 53 from CCD 52 may be employed for the (R) signal or the intensity signal (I) on line 12. The reflective light beam 48 is further reflected from a front surface mirror 54 and passes through a near infrared (NIR) filter 55 to be focused on a second CCD 56. The output of the CCD 56 on line 57 is an NIR signal which may be employed to generate the vegetation ratio NIR/R.

The light passing through the objective lens 47 is also focused on three additional CCDs 58 to 60 to produce the signals Q, U, and V, respectively, shown on lines 61 to 63. In front of the CCDs 58 through 60 there has been placed a horizontal polarization filter, a 45 degree polarization filter, and a circular polarization filter, respectively, which causes the CCDs 58 through 60 to produce the signals Q, U, and V, respectively on line 61 to 63. The signals on line 61 and 63 are applied to the input of block 64 which performs an operation which results in the angle of polarization (AP) on line 13 (produced by taking half the arc tangent of the signal U over Q). In similar manner, the function box 65 takes the three signals on lines 53, 63, and 62 and generates the degree of polarization (DP) shown as being calculated by taking the square root of $Q^2+U^2$ over I to produce the desired degree of polarization output on line 14.

Figure 3:
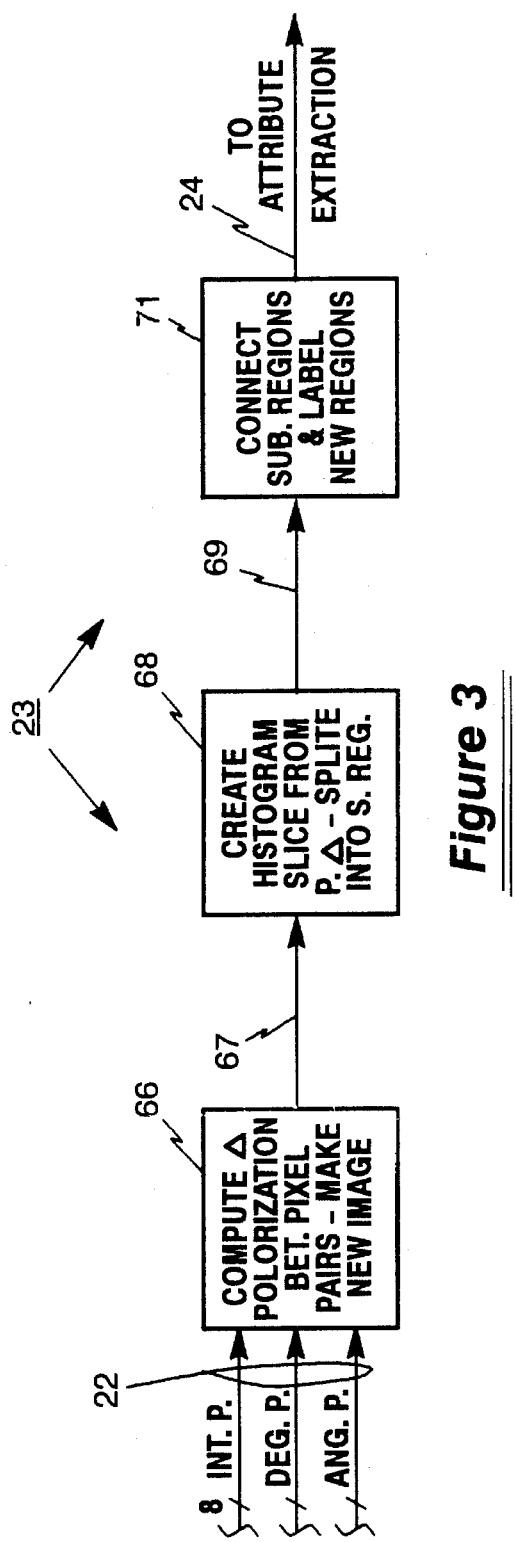
FIG. 3 is a more detailed schematic block diagram of a preferred apparatus and method used for segmentation of image data in FIG. 1.

Refer now to FIG. 3 showing a more detailed schematic block diagram of a preferred apparatus and method used for segmentation of the image data shown in block 23 of FIG. 1. The three inputs on line 22 are designated intensity of polarization, degree of polarization, and angle of polarization and are represented by eight bits each of the 24 bits on line 22. This input information is employed to compute the difference of polarization between pixels pairs and to generate a new image. It will be understood that the new image to be generated does not necessary have to be a complete memory map, but it is most convenient to keep the information in this format. The output of the new image from block 66 on line 67 is applied to a block 68 which performs the function of creating a histogram slice from the polarization difference and also splits the image information into subregions for further analysis. This information on line 69 is applied to a block 71 which analyzes and connects the subregions to form new regions and to label the new regions and also label old regions which are not composed of subregions. The term "labeling" as used herein is broad enough to encompass applying identification indicia which may be alphanumeric, or color or size designations.

Figure 4:
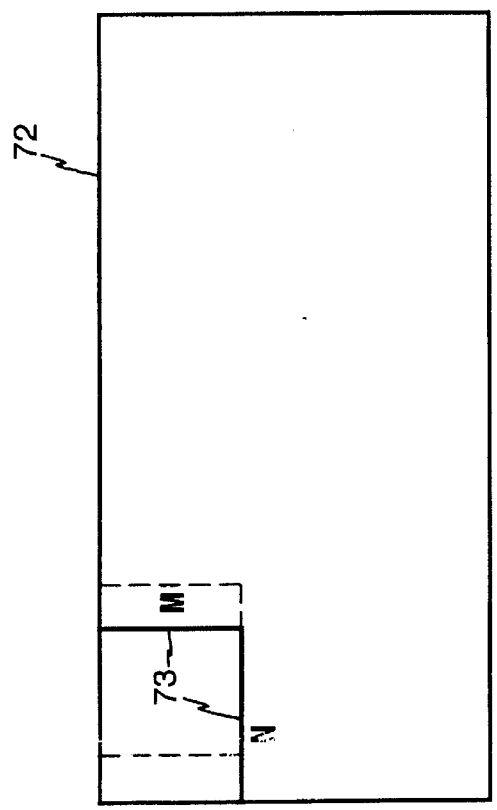
FIG. 4 is a schematic block diagram of a memory map image having a polarization window superimposed thereon.

Refer now to FIG. 4 showing a schematic block diagram of a memory map image 72 having a polarization window 73 superimposed thereon. The rectangular moving window 73 preferably embraces a group of pixels having a dimension M by N which may be a function of the size of the object being examined. The window 73 is stepped one pixel row or one pixel column at a time over the entire memory map 72. To compute the difference in polarization between pixel pairs at each window location each pair of pixels is compared with every other pair of pixels in the window, and the maximum difference between pairs in the window being examined is determined. This difference becomes the difference in polarization (DP) for this particular window location. Thus, the pixel at row 1 column 1 is labeled with the maximum difference between pixel pairs under the window. This continues from column 1 through as many columns as there are in the memory map 72. The window is then stepped down one row and this process is repeated. It will be understood that the last few columns and last few rows cannot be computed as the window 73 cannot step outside of map 72 and they are lost in the new image. Since the window is relatively small for most objects being analyzed, the fringe area that is lost in the new image is insignificant. The polarization difference (PD) for each of the pixel pairs may now be expressed as $PD=\sqrt{\Delta(DP)^2+\Delta(AP)^2}$ where delta $\Delta$ is the difference between pixel pairs.

Figure 5:
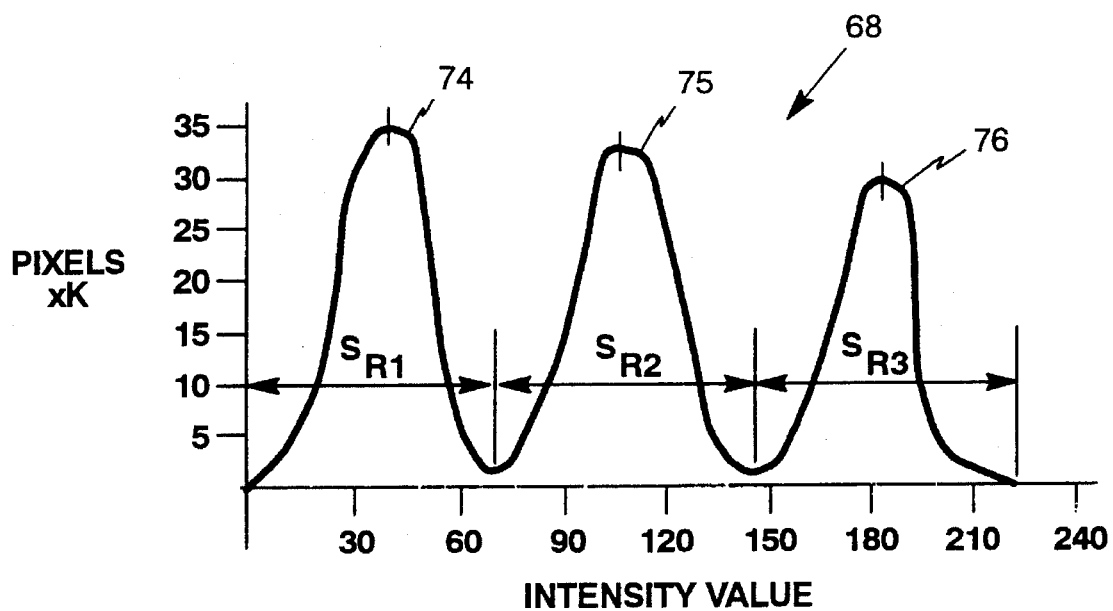
FIG. 5 is a schematic drawing of a waveform used to explain the FIG. 4 operation of histogram slicing employed to generate regions and subregions of objects to be analyzed by their attributes.

Refer now to FIG. 5 showing a schematic drawing of three wave forms 74, 75, and 76 which will be used to explain the operation or function of histogram slicing employed to decompose the polarization difference image into distinct subregions. The subregions noted here are subregion SR1, SR2, and SR3, which are associated respectively with waveforms 74 to 76. The waveforms 74 to 76 are waveforms formed by plotting slices of the subregions the intensity values of the subregions are plotted versus the number of pixels presented by the same intensity in the subregion. For example, the peak of subregion SR1 which contains waveform 74 has a peak of 35 times the factor K pixels at intensity 34. The waveforms are sliced at the troughs between peaks to form the subregions noted. Thus, the subregions are representative of objects sensed in the memory map which have similar polarization attributes.

Figure 6:
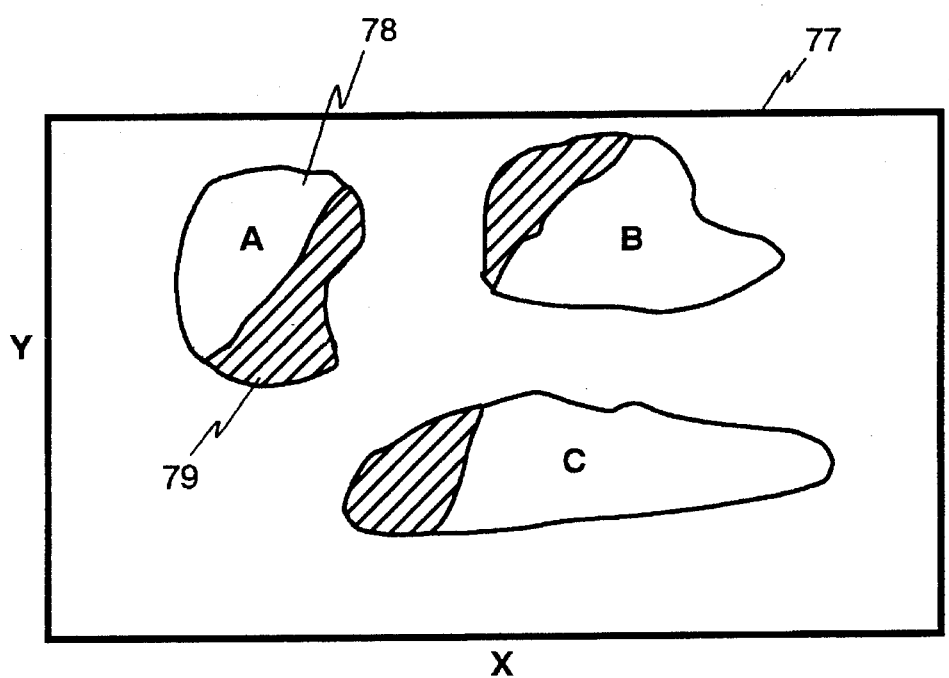
FIG. 6 is a schematic drawing of a memory map image used to explain the FIG. 4 operation of analyzing subregions and connecting the subregions into regions to be defined as object regions for final identification.

Refer now to FIG. 6 showing a schematic drawing of a memory map image used to explain the operation which occurs in block 71 of FIG. 3. The objects A, B, and C in the two dimensional memory map 77 represent regions which have been produced by merging and labeling two or more subregions. For example, the region A like regions B and C comprises two subregions 78 and 79. These newly labeled and merged subregions of regions A, B and C have .attributes of polarization, boundary edge information, size, shape, and intensity which will be used to select the most prominent subregions and perform the aforementioned matching operation.

Having explained a preferred embodiment of the system 10 and modifications thereof with reference to specific operations within the function blocks, it will be understood that other functions and functional blocks may be employed to achieve the selection and definition of attributes used to perform the matching operation which is used to identify objects sensed by the novel polarization sensor.

The operation of the novel polarization diverse infrared object recognition system 10, may be taken airborne and employed to locate objects and features on the ground. In a similar manner the system may be mounted on a moving tractor or moving platform which sprays chemicals. The system is adapted to be used as air to ground as well as ground to air.

The sensor 11 described and explained with reference to FIG. 2 also produces signals on lines 53 and 57 representative of the infrared and near infrared spectral regions. These signals, when used in conjunction with the other signals in FIG. 2, permit the novel automatic object recognition system to remove the background from the image of a scene which contains undesired vegetation. For example, when detected tanks and other vehicles are camouflaged or in a background of vegetation, the present system will completely remove the vegetation or background and leave only the objects of interest.

What is claimed is:

1. An automatic object recognition system, comprising:

a polarization-sensitive infrared sensor for sensing an area containing selective objects to be recognized and identified, said infrared sensor generating a set of output signals representative different polarization features, memory buffer and storage means coupled to the output of said polarization sensitive sensor for storing digital data indicative of polarization features of pixels of an image area being sensed, segmentation means for computing the polarization difference (PD) between said pixels in said image area and generating a new image of said area, means for extracting attributes of regions and subregions of objects sensed in said new image of said area, means for comparing prominent subregions of said objects with models stored in a model based reference library to determine a best match, command control means coupled to said means for comparing prominent subregions for generating signals indicative of a match or no match with models stored in said model based reference library, and utilization means controllable by said command control means upon a match with a stored model.

2. An automatic object recognition system as set forth in claim 1 which further includes means for generating a new object model from said extracted attributes when a no match condition is detected.

3. An automatic object recognition system as set forth in claim 2 which further includes means for labeling and loading said new object model in said model base reference library.

4. An automatic recognition system as set forth in claim 1 which further includes an encoder coupled between said infrared sensor and said memory buffer for converting sensor output analog signals to digital pixel signals stored in a memory map format for display or processing.

5. An automatic object recognition system as set forth in claim i wherein said model based reference library is coupled to said memory buffer and said memory buffer is coupled to a display for displaying data stored in said model base library and/or in said memory buffer.

6. An automatic object recognition system as set forth in claim 5 which further includes means coupling said memory buffer, said segmentation means for computing the polarization difference and said means for extracting attributes of regions and subregions to said model base reference library for storing signals therein for presentation on said display.

7. An automatic object recognition system as set forth in claim 1 wherein said polarization-sensitive infrared sensor is adapted to generate a set of output signals representative of light being sensed in the infrared spectrum between 630 and 870 nanometers in wave length.

8. An automatic object recognition system as set forth in claim 1 wherein said polarization-sensitive infrared sensor is adapted to generate a set of at least three polarizations features including the degree of polarization (DP) and the angle of polarization (AP).

9. An automatic object recognition system as set forth in claim 8 wherein said segmentation means for computing the polarization difference (PD) between pixel pairs comprises means for computing $PD=\sqrt{\Delta(DP)^2+\Delta(AD)^2}$ wherein the term delta $\Delta$ is the difference between pixel pairs.

10. An automatic object recognition system as set forth in claim 9 wherein said segmentation means further comprises means for generating new images from the polarization difference (PD) between pixel pairs.

11. An automatic object recognition system as set forth in claim 10 wherein said segmentation means further includes means for generating histogram slices of said new image of the polarization difference between pixel pairs.

12. The method of recognizing objects that emit infrared radiation, comprising the steps of:

generating a set of analog signals indicative of the degree of polarization, the angle of polarization and the intensity of polarization of a scene being sensed, converting the sets of analog signals to digital values, storing said digital values as pixel values in a memory map of said scene, computing the polarization difference between pairs of pixels in said memory map, generating a new image using the difference between the pixel pairs to form an object image, extracting the attributes of the objects of the new image as regions and subregions of objects, comparing the attributes of said subregions with reference subregions stored in a memory reference library to determine if a match or no match condition exists, and generating control signals to a utilization device if a match occurs.

13. The method as set forth in claim 12 which further includes the step of storing a new model of the object regions in the memory reference library when no match occurs.

\* \* \* \* \*

UNITED STATES PATENT AND TRADEMARK OFFICE
CERTIFICATE OF CORRECTION

PATENT NO. : 5,483,066
DATED : January 9, 1996
INVENTOR(S) : Firooz A. Sadjadi, Stephen M. Sohn It is certified that error appears in the above-indentified patent and that said Letters Patent is hereby corrected as shown below:

Column 6 line 44, "claim i" should be -- claim 1 -- .

Signed and Sealed this

Twenty-sixth Day of March, 1996

Attest:

BRUCE LEHMAN

Attesting Officer

Commissioner of Patents and Trademarks